United States Patent [19]

Palti

[11] Patent Number: 5,513,636
[45] Date of Patent: May 7, 1996

[54] IMPLANTABLE SENSOR CHIP

[75] Inventor: Yoram Palti, Haifa, Israel

[73] Assignee: CB-Carmel Biotechnology Ltd., Israel

[21] Appl. No.: 289,879

[22] Filed: Aug. 12, 1994

[51] Int. Cl.⁶ ............................. A61B 5/00; A61B 5/04
[52] U.S. Cl. .................................... 128/635; 128/642
[58] Field of Search ............................ 128/642, 635, 128/639; 607/116–118

[56] References Cited

U.S. PATENT DOCUMENTS

| | | | |
|---|---|---|---|
| 4,461,304 | 7/1984 | Kuperstein | 128/642 |
| 4,852,573 | 8/1989 | Kennedy | 128/642 |
| 5,101,814 | 4/1992 | Palti . | |
| 5,190,041 | 3/1993 | Palti . | |

OTHER PUBLICATIONS

Yonezawa et al, "Collagen Fibers . . . Activity" Jap. J. Med. Electron. & Biol. Eng. (Japan), vol. 14, No. 5, 1976.
Singhvi, Rahul, et al., "Engineering cell shape and function," *Science*, vol. 264 (1994): 696–698.
Lo, Chun–Min, et al., "Monitoring motion of confluent cells in tissue culture," *Experimental Cell Research*, vol. 204 (1993): 102–109.
Carter, Sherry J., et al., "Comparison of Impedance at the microelectrode–saline and microelectrode–culture medium interface," *IEEE Transactions on Biomedical Engineering*, vol. 39 (1992): 1123–1129.
Fromherz, Peter, et al., "A neuron–silicon junction: a retzius cell of the leech on an isolated–gate field–effect transistor," *Science*, vol. 252 (1991): 1290–1293.
Thomas, C. A. Jr., et al., "A miniature microelectrode array to monitor the bioelectric activity of cultured cells," *Experimental Cell Research*, vol. 74 (1972): 61–66.
Regehr, Wade G., et al., "A long–term in vitro silicon–based microelectrode–neuron connection," *IEEE Transactions on Biomedical Engineering*, vol. 35 (1988): 1023–1032.
Bergveld, Piet, et al., "Extracellular potential recordings by means of a field effect transistor without gate metal, called OSFET," *IEEE Transactions on Biomedical Engineering*, vol. 23 (1976): 136–144.
Jobling, D. T., et al., "Active microelectrode array to record form the mammalian central nervous system in vitro," *Medical and Biological Engineering and Computing*, vol. 19 (1981): 553–560.
Israel, D. A., et al., "Time delays in propagation of cardiac action potential," *Am. J. Phisiol.*, vol. 258 (1990): H1908–H1917.
Israel, David A., et al., "An array of microelectrodes to stimulate and record from cardiac cells in culture," *Am. J. Physiol.*, vol. 247 (1984): H669–H674.

*Primary Examiner*—Lee S. Cohen
*Attorney, Agent, or Firm*—Bryan Cave; David M. Klein

[57] ABSTRACT

An implantable sensor chip, which is preferably small enough to be injected through a hypodermic needle, includes a base constructed of an electrically insulating material, and at least one sensor for generating an output signal in the presence of a constituent or the existence of a condition. The sensor includes an electrically conductive lead mounted on an upper surface of the base. One end of the lead includes a conducting plate. An insulating layer is mounted on the upper surface of the base over the electrically conductive lead and the conducting plate, sealing the electrically conductive lead and conducting plate between the insulating layer and the base. The insulating layer has an aperture extending therethrough for exposing a portion of the conductive plate. At least one cell sealingly covers the exposed portion of the electrically conductive plate with the cell in electrical communication with the plate. The cell generates an electrical signal in response to the presence of the constituent or the existence of the condition. The electrical signal is conducted by the lead to an output end of the lead. The output signal is amplified by an amplifier, and may be processed further either at the skin surface, on the sensor chip, or by another implanted processing means. The sensor chip preferably includes a plurality of individual sensors constructed thereon.

10 Claims, 2 Drawing Sheets

IMPLANTABLE SENSOR CHIP

BACKGROUND OF THE INVENTION

1. Field of the Invention

The present invention relates to an implantable sensor chip for detecting a constituent level or condition, and more particularly to a sensor chip which includes living cells sensitive to the constituent level or condition, which are grown on a fabricated sensor substrate.

2. Description of the Related Art

Normally, cells have a constant potential difference across the membrane of the cell. Many types of living cells, however, generate electric signals under particular conditions or in the presence of particular constituents to which the cells are sensitive. These signals usually appear as voltage or potential spikes which are of relatively short duration. The amplitude of these voltage spikes is on the order of 0.1 V and the duration of the spikes varies from about 1 ms to 1 s. These electrical signals or spikes can be directly related to a major function of the cells, for example, in nerve cells, or they can be caused by some other activity, for example, cardiac muscle activity.

When these signals appear across the cell membrane, they may be recorded by introducing a first microelectrode into the cell, by providing a second electrode in the medium surrounding the cell, and by measuring the potential difference between the electrodes. However, the electric potential or electric field generated by an individual cell undergoing voltage spikes as recorded by external electrodes tends to be very small. Therefore, in practice, only fields generated by relatively large masses of cells that are firing simultaneously may be recorded, i.e., EEG, ECG, EMG, etc.

Commonly owned U.S. Pat. Nos. 5,101,814 and 5,190,041, and U.S. patent application Ser. No. 08/077,893, now U.S. Pat. No. 5,368,028, the contents of which are incorporated herein by reference, disclose methods by which the electrical activity of living cells encapsulated in a biocompatible semi-permeable membrane may be measured. This electrical activity may be used to determine the concentration of various constituents or conditions in the medium that surrounds the cells or capsule. These electrical signals can be measured by electrodes within the membrane capsule, or in its vicinity outside the capsule. By implanting the capsule under a patients skin, it is impossible to determine the concentration of a predetermined constituent (e.g., glucose level) or a predetermined condition (e.g., blood pressure) in the region (e.g., adjoining tissue or blood vessel) in which the capsule is implanted.

All of the prior art devices measure the combined electrical activity of large cell masses. An object of the present invention is to enable individual cells rather than groups of cells to be used for detection of physical conditions or constituents by detecting the electrical signals generated by the individual cells. A further object of the invention is to detect the electrical signals without penetrating the cells with micro electrodes, which is not practical for long term in-vivo measurements.

SUMMARY OF THE INVENTION

The present invention is an implantable sensor chip which comprises a base constructed of an electrically insulating material, and at least one sensor for generating an output signal in the presence of a constituent or the existence of a condition. The sensor includes an electrically conductive lead mounted on an upper surface of the base. An insulating layer is mounted on the upper surface of the base over the electrically conductive lead whereby the electrically conductive lead is sealed between the insulating layer and the base. The insulating layer has an aperture extending therethrough for exposing a portion of the electrically conductive lead. At least one cell, and preferably only one cell, covers and seals the exposed portion of the electrically conductive lead with the cell in electrical communication with the lead. The cell generates an electrical signal in response to the presence of the constituent or the existence of the condition. The electrical signal is conducted by the lead to an output end of the lead. The sensor chip is preferably small enough to be implantable through a hypodermic needle. The output signal is amplified by an amplifier, and may be processed further either at the skin surface, on the sensor chip, or by another implanted processing means.

If desired, a conductive plate may cover the exposed portion of each electrically conductive lead with a portion of the conductive plate exposed in the aperture. The conductive plate is constructed of an electrically conductive material, and the cell covers and seals the exposed portion of the conductive plate in electrical communication therewith. In this embodiment, the electrical signal from the cells is conducted by the conducting plate to the lead.

The sensor chip is surrounded by a semi-permeable capsule having a molecular weight cutoff which will enable nutrients and excretions to migrate to and from the cells, while preventing the larger molecules from attacking the sensor cells.

Once the sensor chip has been fabricated without the cells, the cells are grown over the apertures. The conductive plates act as electrodes and record the electric potential changes associated with the cell's activity (relative to a reference electrode). Thus, the present invention enables individual cells to be used as sensors for detection of physical conditions or constituents.

DESCRIPTION OF THE PREFERRED EMBODIMENT

Figure 1:
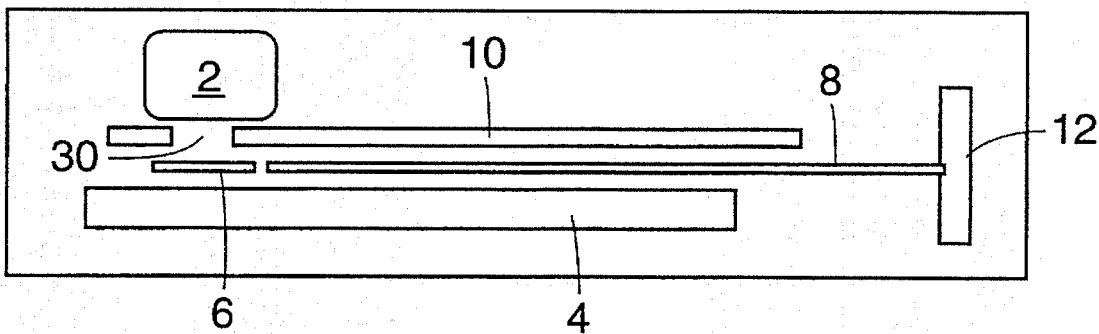
FIG. 1 is a side view of the sensor chip of the invention.
Figure 2:
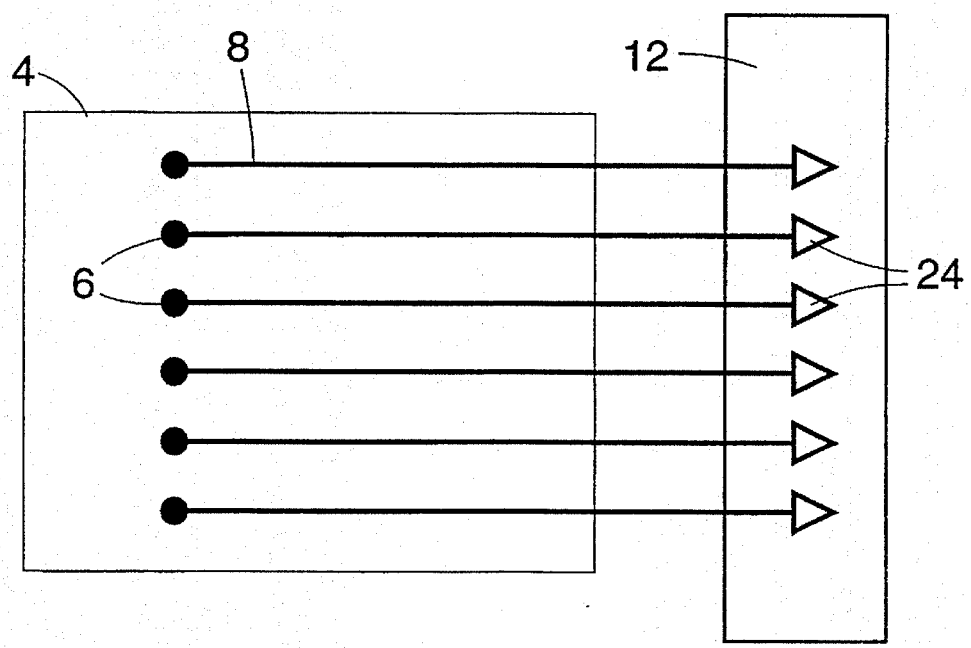
FIG. 2 is a top view of the sensor chip of the invention, sensors on the chip.

As shown in FIGS. 1–2, the present invention is an implantable sensor chip in which one or more discrete sensors is mounted on the chip for sensing a constituent level or condition. Each individual sensor on the sensor chip includes one cell 2 of any type which generates an electrical signal, i.e., a voltage or current, in response to the presence of a particular constituent or condition in a medium surrounding the cell 2. One such cell type for detecting blood-glucose levels is disclosed in the aforementioned commonly owned U.S. Pat. Nos. 5,101,814 and 5,190,041, and U.S. patent application Ser. No. 08/077,893.

The sensor is preferably fabricated using conventional semiconductor fabrication techniques, although any appropriate method of manufacture may be utilized. The sensor includes a base 4 which is preferably constituted of an electrically insulating material, e.g., silicon or a non-conducting glass. Base 4 is preferably, though not necessarily, transparent and has a thickness preferably less than 1 mm. It is preferable that base 4 be transparent in order to view the living cells 2 which are to be grown on the sensor chip. Otherwise, base 4 may have any appropriate shape or dimensions provided that it can perform the functions described herein. If the sensor is to be implanted using a hypodermic needle, it is preferred that the total size of the sensor be on the order of 0.2–0.55 mm in width and 0.3–5.0 mm in length.

A conducting plate 6 is provided under each cell 2 to make electrically conductive contact with the cell 2. Each conducting plate 6 acts as an electrode which detects the electrical signal generated by the cell 2, in conjunction with a second electrode (not shown) located in the medium surrounding cell 2. The cell 2 adheres to the conducting plate 6 and to the insulating layer 10 (described in detail below).

Conducting plates 6 are in electrical contact with leads 8 which are fabricated on the base 4. The electrical signal generated by each cell 2 is transmitted by a conducting plate 6 under the cell 2 to a lead 8 associated with that cell, which in turn conducts the electrical signal generated by the cell 2 to an electronic processing system 12. The conducting plates 6 can be fabricated from any bio-compatible (non-toxic to and compatible with living cells for long periods of time) electrically conductive material, i.e., platinum, gold, conducting silicone, etc. The conducting plates 6 may be round, rectangular, or any other shape. Typically, the conducting plates 6 would be about 2.0–10.0 microns in width (or radius) and less than about 0.1 micron thick. When a cell 2 is grown over each conducting plate 6, the conducting plate 6 must be completely covered by the cell 2 or the insulating layer 10. Otherwise, the conducting plate 6 would be exposed to the medium surrounding the cells 2 and a partial or complete short circuit would be formed between the conducting plates 6 and the second electrode (not shown). Thus, any signal generated by the cell 2 over the exposed conducting plate would not be accurately detectable. Accordingly, the conducting plates 6 must be completely covered by the cells 2 alone or in combination with insulating layer 10.

Leads 8 are preferably fabricated on the base 4 before or at the same time as the conducting plates 6. The leads 8 are made from an electrically conductive material, such as metal or a conducting silicone, and may be made from the same material as the conductive plates 6 provided that the material is bio-compatible. Leads 8 are preferably narrow in width, so that the leads do not contact each other, and each lead is in contact with only one conductive plate 6. This allows numerous sensors to be fabricated on the small surface area of the chip. The leads 8 are also preferably not so thick as to interfere with viewing the cells. The width of each lead 8 is preferably on the order of about 1.0–5.0 microns and the thickness of each lead 8 less than about 0.1 micron. As previously mentioned, each lead 8 conducts the electrical signal generated by one sensor cell 2 to an electronic processing system 12 either on the sensor device itself, or external to the device.

Insulating layer 10 is fabricated over leads 8 and preferably provides a substantially continuous insulating layer between the leads 8 and the medium surrounding the cells. Insulating layer 10 includes an aperture 30 over each conducting plate 6 which at least partially exposes the conducting plate 6 in order that a cell 2 may be grown in electrical contact with the conducting plate 6. The electrical contact may be direct or via fluid that may fill the space in between the cells 2 and the conducting plates 6 either from excretions from the cell 2 or with a growing medium during the growing process. In an alternative embodiment, conducting plates 6 may be eliminated, and insulating layer 10 may include an aperture over each lead 8 which at least partially exposes the lead 8 in order that a cell 2 may be grown directly in contact with the lead 8.

The insulating layer 10 is preferably fabricated from silicon, a non-conductive glass, or any other bio-compatible non-electrically conductive material from which microchips may be fabricated. The insulating layer 10 is preferably transparent and has a thickness on the order of about 1.0–10.0 microns which enables the cells 2 which are grown on this layer to be viewed.

The exposed upper surface of the insulating layer 10 on which the cells 2 are to be at least partially grown (part of each cell grows on the conducting plate 6, and part of the cell grows on the insulating layer 10) should be processed so that the cells grow on this layer and tend to strongly and sealingly adhere to it. For example, the upper surface of the insulating layer 10 near the apertures 30 for the conducting plates 6 could be made rough or course by chemical etching, by electric discharge, coating by polylysine or by any conventionally known method. The strong adherence and seal between the cell 2 and the insulating layer 10 prevents the electrical signal from the cell 2 from being attenuated by short circuiting between the cell 2 or conducting plate 6 and the medium surrounding the cell 2.

The entire sensor, which includes base 4, conducting plates 6, leads 8, insulating layer 10 and one or more living cells 2 which are grown over the conducting plates 6 and insulating layer 10, is fixed within a capsule 14 that is implanted in a patient, animal, tissue or fluid. The implantation can be subcutaneous, intraperitoneal, etc. The capsule 14 serves as a barrier that prevents the cells 2 from migrating away from the sensor chip or from being dislodged from the sensor chip, while enabling nutrients, excretions, and other constituents necessary for the survival of the cell to diffuse to and from the cell. The capsule 14 also prevents antibodies and other large molecules or cells from entering the sensor and causing, for example, immunological reactions. The use of a capsule 14 surrounding the sensor chip also enables the use of tumor cells (preferably non-malignant) as sensor cells 2.

Figure 3:
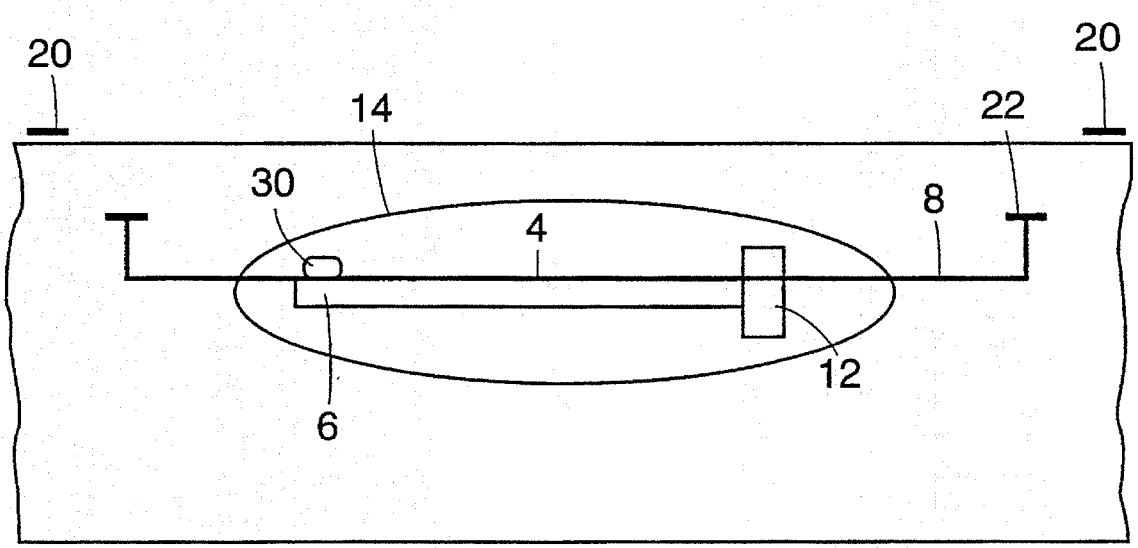
FIG. 3 shows the sensor chip of the invention mounted in a semi-permeable capsule and implanted.

The capsule is preferably a small diameter cylinder having an outer diameter on the order of about 200–400 microns, and semipermeable walls about 50.0–100.0 microns thick. The ends of the capsule 14 are closed so that the capsule is shaped like an elongated pellet, as shown in FIG. 3. The semi-permeable membrane is made, for example, of PSF (polysulfone) and PVC/PAN (polyvinylchloride/polyacylonitrile) or a polyvinyl chloride acrylic copolymer suitable for preventing passage therethrough of molecules having a molecular weight greater than about 30,000–50,000. This molecular weight cutoff will enable nutrients and excretions to migrate to and from the cells 2, while preventing the aforementioned larger molecules from attacking the sensor cells 2.

The sensor preferably includes an electronic processing system 12 which receives the cell electrical signals through the leads 8. The processing system 12 amplifies the electrical signal from the cells 2 and may filter the signals as well, using a conventional electrical filter 24. Amplification is preferably accomplished by a conventional differential operational amplifier, although any conventional amplification system may be used.

The output from the processing system 12 may be used in one of several ways: Firstly, the signal from the sensor can be fed by conventional electrical leads to the controller of an implanted drug delivery system, for example a drug delivery system of the type disclosed in commonly-owned U.S. patent application Ser. No. 08/266,736, now U.S. Pat. No. 5,474,552, entitled Implantable Drug Delivery Pump. The controller will utilize the signals to determine the drug delivery rate.

The amplified signal from the sensor chip may be transmitted to the external surface of the subject in which the sensor is implanted where the signals will be received by an external electrical pickup device. This may be done in one of several ways. First, the amplified signal may be transmitted to the surface by conventional electric leads which penetrate the skin. Second, the amplified signal may be transmitted to the surface by capacitive or electromagnetic coupling, in which a pickup device including a coil of wire or the like is located outside the skin of the subject and picks up the signal generated by the sensor by coupling to it. Finally, the output signal from the sensor chip could be used to generate a current or potential field in the conductive tissue volume surrounding the sensor chip capsule by means of external electrodes 22. In this embodiment, surface conductive electrodes 20 may be used to pick up the electrical signal from below the skin surface. It will be appreciated that amplification is necessary only for the purpose of improving the output signal strength from the sensor. If a pickup device is used which is sensitive enough to pick up the non-amplified signal, then no amplification is necessary.

The power for the amplifier and other signal processing equipment may be provided by either an implanted battery (which would make injection of the sensor difficult or impossible) or preferably by induction or capacitive coupling from an energy source positioned over the implant outside the skin surface. If the sensor chip is used in conjunction with a drug delivery system, power for the sensor may be provided by the drug delivery system.

While the output signals from the sensor are preferably amplified on the sensor chip, additional signal processing of the output signals for analyzing and interpreting the output signals, in terms of the concentration of the constituent being measured or of a condition, may be done either on the sensor chip, or elsewhere, i.e., by external processing means above the skin, or in a processor in a drug delivery system. The simplest interpretation of the output signal would utilize the frequency and/or amplitude of the voltage spikes generated by the cells as representing the constituent level or condition. More complex analysis could take into account the rate of frequency change, characterization of firing burst duration or interval, etc.

Since the sensor chip preferably includes more than one individual sensor, each of the outputs is preferably amplified as discussed above. A single amplifier may be used, and the sensor outputs may be multiplexed into the amplifier, or a separate amplifier may be provided for each sensor output. The amplified outputs are then multiplexed together, and the multiplexed output is transmitted to the external surface. The multiplexed signal is also preferably digitized prior to being transmitted to the surface. A synchronization signal may be included with the digitized output data so that a processor on the surface will be able to properly demultiplex the signal transmitted to the surface. In the alternative, the multiplexor on the sensor chip may be synchronized to a signal generated at the surface and transmitted to the sensor chip.

Once the sensor chip has been fabricated, including the base 4, the leads 8, the conducting plates 6, and the insulating layer 10, the sensing cells 2 are "plated" on the chip, at least over the apertures 30 in the insulating layer 10. The sensor chip is then flooded with tissue culture medium and incubated until the cells adhere to the insulating layer 10 around the apertures 30. The cell density is preferably high enough that most of the conducting plates 6 are covered by cells 2. The electric output from each individual sensor on the sensor chip is then measured in the presence of the constituent or condition to which the cells 2 are sensitive. If the electric activity of a sufficient number of cells 2 is recorded, the sensor chip with the cells 2 are sealed in the capsule and the sensor chip is ready for use. It will be appreciated that not every individual sensor on each sensor chip will necessarily be functional, since some cells 2 may not adhere well or function properly when the sensor chip is completed. Nonetheless, each sensor chip preferably includes a number of individual sensors so that the sensor chip will operate effectively even if some of the sensors do not operate properly.

Although the present invention has been described in detail with respect to certain embodiments and examples, variations and modifications exist which are within the scope of the present invention as defined in the following claims.

I claim:

1. An implantable sensor chip, which comprises:
   a) a base constructed of an electrically insulating material; and
   b) at least one sensor for generating an output signal in the presence of a constituent or the existence of a condition in a region in which the sensor chip is implanted, the sensor comprising:
      I. an electrically conductive lead mounted on an upper surface of the base, the conductive lead having an output end;
      II. an insulating layer mounted on the upper surface of the base over the electrically conductive lead and sealing the electrically conductive lead between the insulating layer and the base, the insulating layer comprising an aperture extending therethrough for exposing a portion of the electrically conductive lead; and
      III. at least one living cell sealingly covering the exposed portion of the electrically conductive lead with the cell in electrical communication with the lead, the cell generating an electrical signal in response to the presence of the constituent or the existence of the condition, the electrical signal being conducted by the lead to the output end of the lead as the output signal.

2. The sensor chip according to claim 1, wherein each sensor further comprises a conductive plate covering the exposed portion of the electrically conductive lead, the conductive plate constructed of an electrically conductive material, a portion of the conductive plate exposed in the aperture, the cell sealingly covering the exposed portion of the conductive plate in electrical communication therewith; wherein the electrical signal is conducted by the conducting plate to the lead.

3. The sensor chip according to claim 2, which comprises a plurality of sensors.

4. The sensor chip according to claim 3, further comprising an amplifier electrically connected to the output end of the lead for amplifying the output signal form each sensor.

5. The sensor chip according to claim 4, further comprising a semi-permeable capsule surrounding the base and the sensors.

6. The sensor chip according to claim 3, further comprising a semi-permeable capsule surrounding the base and the sensors.

7. The sensor chip according to claim 2, further comprising an amplifier electrically connected to the output end of the lead for amplifying the output signal from the sensor.

8. The sensor chip according to claim 1, which comprises a plurality of sensors.

9. The sensor chip according to claim 1, further compris ing an amplifier electrically connected to the output end of the lead for amplifying the output signal from the sensor.

10. The sensor chip according to claim 1, further comprising a semi-permeable capsule surrounding the base and the sensor.

* * * * *